United States Patent [19]

van Andel

[11] Patent Number: Plant 5,506

[45] Date of Patent: Jul. 2, 1985

[54] CARNATION NAMED MUDAVE

[75] Inventor: Jacob van Andel, Aalsmeer, Netherlands

[73] Assignee: B. V. Handelskwekerij, M. C. van Staaveren, Aalsmeer, Netherlands

[21] Appl. No.: 556,459

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of miniature white carnation plant characterized by its continuous production of small white blooms of somewhat smaller than normal size and with a larger number of flowers appearing on each flowering stem.

1 Drawing Figure

BACKGROUND OF THE NEW PLANT

This new carnation cultivar was found as a seedling of unknown parentage growing among a collection of miniature carnations maintained in greenhouse for breeding purposes at Aalsmeer, The Netherlands, this particular plant being selected by me because of its apparently profuse production of small white flowers with many more flowers on each flower stem as compared with the common miniature carnation varieties. I propagated this new plant at Aalsmeer by means of cuttings to observe its growth and flowering characteristics and the product appeared so favorable that I continued propagation by cuttings through several successive generations and observed that its favorable growth and flowering characteristics were fully retained from generation to generation and appeared to be firmly fixed.

DESCRIPTION OF THE DRAWING

My new carnation plant is illustrated by the accompanying full color photographic drawing which shows buds and flowers in various stages of growth as they appear on tall flowering stems.

DESCRIPTION OF THE NEW PLANT

The following is a detailed description of my new miniature carnation plant based upon observations of plants grown in greenhouse and observed during the early Summer of 1983, the color designations being according to The R.H.S. Colour Chart published by The Royal Horticultural Society of London, England.

THE PLANT

Origin: Seedling.
Parentage: Unknown.
Classification:
- *Botanic.*—*Dianthus caryophyllus* Hybrid.
- *Commercial.*—Miniature carnation.

Form: Tall bush.
Height: Various depending on season.
Growth: Upright and of medium strength with normal branching.
Foliage:
- *Quantity.*—Medium.
- *Size of leaf.*—Medium.
- *Shape of leaf.*—Oblong.

- *Texture.*—Smooth.
- *Color.*—Upper side — Grey/Green. Under side — Grey/Green.

THE BUD

Size: Medium.
- *Diameter.*—About 10 mm.
- *Length.*—About 20 mm.

Shape: Pointed ovoid becoming cylindrical as sepals reach dividing stage.
Opening rate: Moderate.
Color of petals: When sepals first divide and when petals begin to unfurl — White.
Sepals:
- *Shape.*—Oblong with acute tip. When flowers open, sepals stand up.
- *Color.*—Inside — Grey/Green. Outside — Grey/-Green.

Calyx:
- *Shape.*—Funnel-shaped.
- *Size.*—Long.
- *Aspect.*—Smooth.
- *Splitting.*—The calyx does not split.

Peduncle:
- *Length.*—Various but generally short.
- *Character.*—Rigid.
- *Color.*—Grey/Green.

THE FLOWER

Blooming habit: Continuous.
Size of bloom: Small.
- *Diameter.*—About 35 mm.
- *Depth.*—About 10 mm.

Shape:
- *When bloom first opens.*—Flat.
- *When bloom matures.*—Slightly domed.

Petalage:
- *Number of petals.*—About 30.
- *Arrangement.*—Overlapping.
- *Shape.*—Fan-shaped with toothed margin.
- *Texture.*—Soft.
- *Appearance.*—Shiny.
- *Color.*—Outer and inside petals: Top side — Body: R.H.S. 155C. Base: Pale Green. Reverse side — R.H.S. 155C. Colors are the same for all seasons.

Flower stem:
- *Length.*—Depending on season.

*Character.*—Of medium strength and upright growth.

*Color.*—Grey/Green.

Persistence: The flowers hang on and dry.

Fragrance: Weak.

Disease resistance: Less susceptible to fusarium oxysporum as observed in the district of Aalsmeer, The Netherlands.

Lasting quality:

*On plant.*—About 15 days.

*As cut flower.*—About 8 days.

REPRODUCTIVE ORGANS

Stamens:

*Number.*—Medium.

*Anthers.*—Color: Cream.

*Filaments.*—Color: White.

*Pollen.*—No pollen present.

Pistils:

*Number.*—One.

*Styles.*—Length: Approximately 25 mm. Color: White.

*Stigma.*—Color: White.

This miniature carnation plant has the advantage of fast and excellent flower production and is particularly distinguished by bearing a larger number of smaller flowers per flowering stem as compared with common miniature varieties.

I claim:

1. A new and distinct miniature carnation plant, substantially as herein shown and described, characterized by its fast and profuse production of small white flowers which are borne in greater number on each flowering stem than is normal for common miniature varieties.

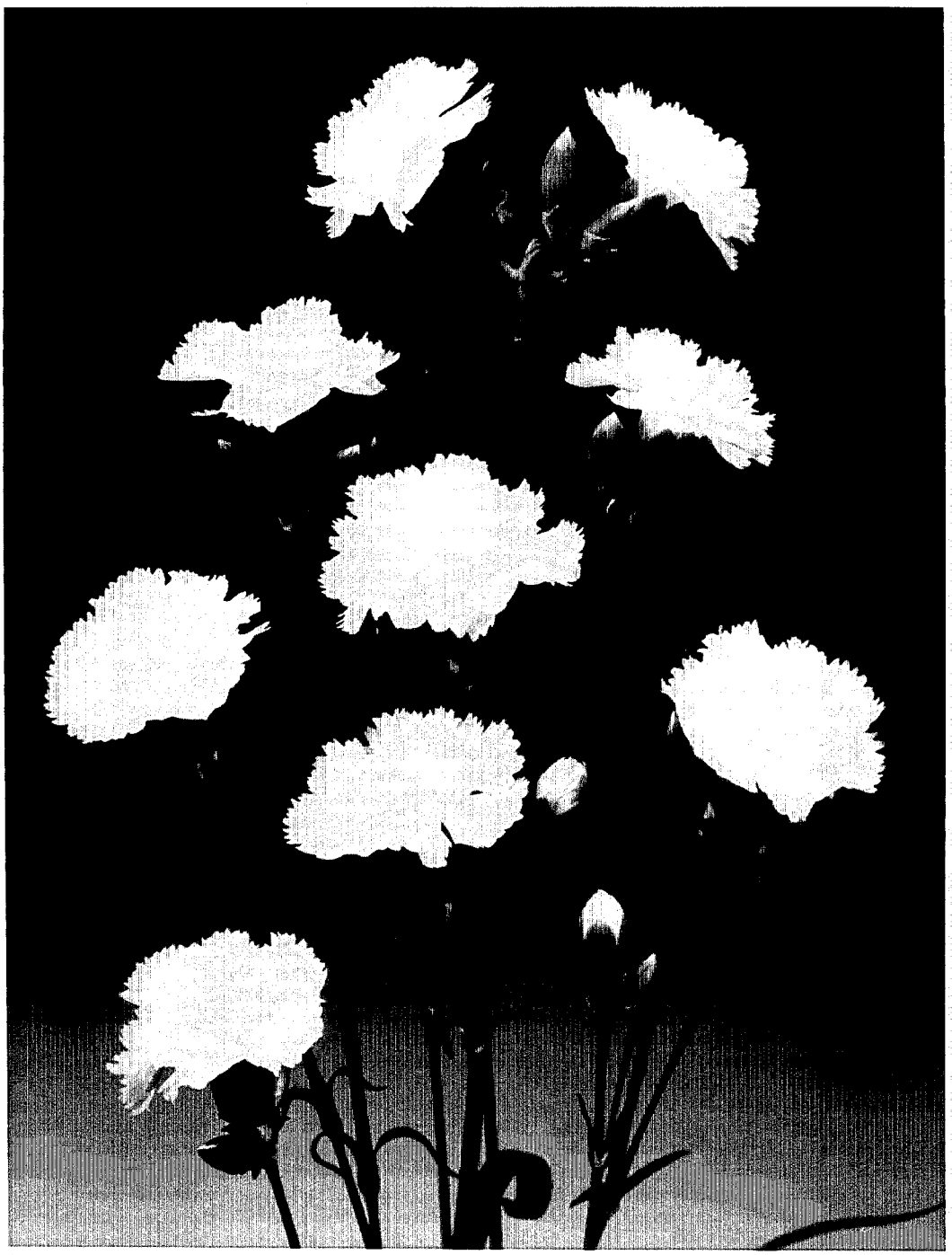

* * * * *